(12) United States Patent
Wei

(10) Patent No.: US 6,325,512 B1
(45) Date of Patent: Dec. 4, 2001

(54) RETINAL TRACKING ASSISTED OPTICAL COHERENCE TOMOGRAPHY

(75) Inventor: Jay Wei, Fremont, CA (US)

(73) Assignee: Carl Zeiss, Inc., Thornwood, NY (US)

( * ) Notice: Subject to any disclaimer, the term of this patent is extended or adjusted under 35 U.S.C. 154(b) by 0 days.

(21) Appl. No.: 09/703,044

(22) Filed: Oct. 31, 2000

(51) Int. Cl.[7] .................................................. A61B 3/10
(52) U.S. Cl. .......................................................... 351/209
(58) Field of Search .................................... 351/208, 209, 351/205, 210, 214, 221; 382/103, 131

(56) References Cited

U.S. PATENT DOCUMENTS

| | | | |
|---|---|---|---|
| 5,321,501 | 6/1994 | Swanson et al. | 356/345 |
| 5,459,570 | 10/1995 | Swanson et al. | 356/345 |
| 5,506,634 | 4/1996 | Wei et al. | 351/221 |
| 5,644,642 * | 7/1997 | Kirschbaum | 382/131 |
| 5,767,941 | 6/1998 | Ferguson | 351/206 |

OTHER PUBLICATIONS

"400–Hz mechanical scanning optical delay line" by K. F. Kwong et al., *Optics Letters*, vol. 18, No. 7, Apr. 1, 1993, pp. 558–560.

"High–speed–phase– and group–delay scanning with a grating–based phase control delay line" by G. J. Tearney et al., *Optics Letters*, vol. 22, no. 23, Dec. 1, 1997, pp. 1811–1813.

* cited by examiner

*Primary Examiner*—George Manuel
(74) *Attorney, Agent, or Firm*—Michael B. Einschlag

(57) ABSTRACT

One embodiment of the present invention is an optical coherence tomography ("OCT") application apparatus that performs an OCT application on an object. The OCT application apparatus includes: (a) an OCT scanning apparatus which outputs a beam of OCT scanning radiation; (b) an active tracking system that generates and projects a beam of tracking radiation onto a region including a reference tracking feature, which active tracking system includes a tracking optical system that is disposed to intercept the beam of tracking radiation and the beam of OCT scanning radiation; and (c) wherein the active tracking system analyzes tracking radiation reflected from the region to detect movement of the object, and to generate a tracking signal which directs the tracking optical system to follow the movement of the object. In one embodiment of the present invention, the OCT application comprises forming an OCT scan image of the object, for example and without limitation, a retina of an eye.

44 Claims, 3 Drawing Sheets

RETINAL TRACKING ASSISTED OPTICAL COHERENCE TOMOGRAPHY

TECHNICAL FIELD OF THE INVENTION

The present invention pertains to method and apparatus for performing an optical coherence tomographic examination of tissue such as an eye. In particular, the present invention relates to method and apparatus for performing an optical coherence tomographic examination of an eye using an active tracking system to lock an optical coherence tomography ("OCT") scanning beam on desired features in retinal tissue for use, for example, in imaging retinal tissue, measuring retinal and retinal nerve fiber layer thickness, mapping the topography of the optic nerve head, and so forth.

BACKGROUND OF THE INVENTION

As is well known, an optical coherence tomography ("OCT") apparatus (for example, as disclosed in U.S. Pat. No. 5,321,501 ("the '501 patent")) is an optical imaging apparatus that can perform micron-resolution, cross-sectional imaging (also referred to as tomographic imaging) of biological tissue. As is also well known, to make measurements along an axial direction (i.e., into the biological tissue): (a) radiation is directed to, and reflected by, a reference mirror located in one arm (a reference arm) of a Michelson interferometer (the position of the reference mirror is scanned); and (b) in a second arm (a sample arm) of the Michelson interferometer, radiation is directed to, and scattered by, the biological tissue. Whenever the optical path difference of radiation in the two arms of the Michelson interferometer equals, or is less than, the optical coherence length of the radiation transmitted into the interferometer from a source, an optical interference signal can be detected. As disclosed in the '501 patent, a cross-sectional image of the tissue is formed by combining data from serial axial scans.

The length of time it takes to produce a tomographic image is limited by several factors: (a) the scan speed of the reference mirror in the reference arm used to obtain measurements in the axial direction; (b) the transverse scan speed of deflectors used to acquire serial axial scans; (c) signal-to-noise limits related to image quality; and (d) the speed of electronics, and any associated computer, in sampling analog OCT signals and transforming them into a pseudo color, or gray scale, image. However, in general, as the scan speed of the reference mirror goes up, the signal-to-noise ratio goes down; thereby adversely affecting the image quality. On the other hand, when imaging tissue in an eye, one is constrained to obtain images rapidly to avoid problems caused by eye movement.

At present, the scan speed of the reference mirror is a limiting factor in OCT image acquisition. To understand this, refer to U.S. Pat. No. 5,459,570 ("the '570 patent") where the reference mirror is moved by a PZT actuator. Although the scan speed of a PZT actuator can be as high as several KHz, the scan range is limited to the micron range, which micron range is not practical for in vivo human eye diagnosis where a scan range of a couple of millimeters is required for clinical use. Although the required several millimeter scan range can be obtained by mounting a retro-reflector on one end of an arm that is scanned by a galvanometer, the scan speed is limited to about a couple hundred hertz (this scan method is currently employed in a commercially available OCT scanner device made by Zeiss Humphrey Systems of Dublin, Calif.).

A scan device in an OCT system that provides a two to four KHz scan speed with a useful scan range was disclosed in an article entitled "High-speed phase- and group-delay scanning with a grating-based phase control delay line" by G. J. Tearney et al. in *Optics Letters,* Vol. 22, No. 23, Dec. 1, 1997, pp. 1811–1813, which scan device was based on a phase ramping delay line principle disclosed in an article entitled "400-Hz mechanical scanning optical delay line" by K. F. Kwong et al. in *Optics Letters,* Vol. 18, No. 7, Apr. 1, 1993, pp. 558–560. A disadvantage of the scan device disclosed in the G. J. Tearney et al. article is that it is easily worn out, and there is an upper limit light power allowed for safe use in in-vivo human eye diagnosis. However, as pointed out above, with increasing scan speed, the signal-to-noise ratio will be reduced, and image quality will deteriorate.

Although OCT scan data can be used to provide tomographic images of tissue such as an eye, the OCT data obtained has many uses other than in providing an image. For example, applications of OCT data include measuring retinal and retinal nerve fiber layer thickness, mapping the topography of the optic nerve head, and so forth. However, in these applications, similar problems arise, i.e., how to obtain data having acceptable signal-to-noise ratios while taking into account movement of the tissue. In light of the above, there is a need for a method and apparatus that can obtain high quality OCT data, for example, to form tomographic scan images, while taking into account the issue of, for example, patient movement.

SUMMARY OF THE INVENTION

Embodiments of the present invention advantageously satisfy the above-identified need in the art, and provide method and apparatus for performing optical coherence tomography ("OCT") applications. Specifically, a first embodiment of the present invention is an OCT application apparatus that performs an OCT application on an object, which OCT application apparatus comprises: (a) an OCT scanning apparatus which outputs a beam of OCT scanning radiation; (b) an active tracking system that generates and projects a beam of tracking radiation onto a region including a reference tracking feature, which active tracking system includes a tracking optical system that is disposed to intercept the beam of tracking radiation and the beam of OCT scanning radiation; and (c) wherein the active tracking system analyzes tracking radiation reflected from the region to detect movement of the object, and to generate a tracking signal which directs the tracking optical system to follow the movement of the object. In one embodiment of the present invention, the OCT application comprises forming an OCT scan image of the object, for example and without limitation, a retina of an eye.

DETAILED DESCRIPTION

In accordance with an embodiment of the present invention, a high resolution, tomographic image of features of, for example, a human eye is obtained by performing a relatively slow optical coherence tomography ("OCT") scan. For example, some patients can keep an eye open for as long as ten (10) seconds. Advantageously, in accordance with this embodiment of the present invention, the signal-to-noise ratio of images generated by performing such a slow scan is higher that that obtained using relatively a rapid scan characteristic of the prior art since the signal-to-noise ratio of the OCT image increases with the square root of the speed of the scan.

To perform a relatively slow scan in accordance with one embodiment of the present invention, a beam of OCT scanning radiation is locked onto a reference tracking feature to avoid artifacts that might occur due to patient eye movement. In a preferred embodiment of the present invention, the OCT scan beam is locked onto the reference tracking feature by an active tracking system, which active tracking system utilizes a reflectance characteristic of the reference tracking feature to provide a tracking signal. Advantageously, such an active tracking system can operate at rates which are required for in-vivo human eye tracking rates, i.e., at rates as high as several KHz.

Although an embodiment of the present invention is described with reference to providing an OCT tomographic image, those of ordinary skill in the art will readily appreciate that the present invention is not limited to embodiments wherein an OCT tomographic image is produced. In particular, it is within the scope of the present invention to include embodiments wherein OCT data is obtained for uses other than and/or in conjunction with an image such as, for example and without limitation, measuring retinal and retinal nerve fiber layer thickness, mapping the topography of the optic nerve head, and so forth. Thus, an apparatus to perform any of these applications will be referred to herein as an OCT application apparatus and a method to perform any of these applications will be referred to herein as an OCT application method.

Figure 1:
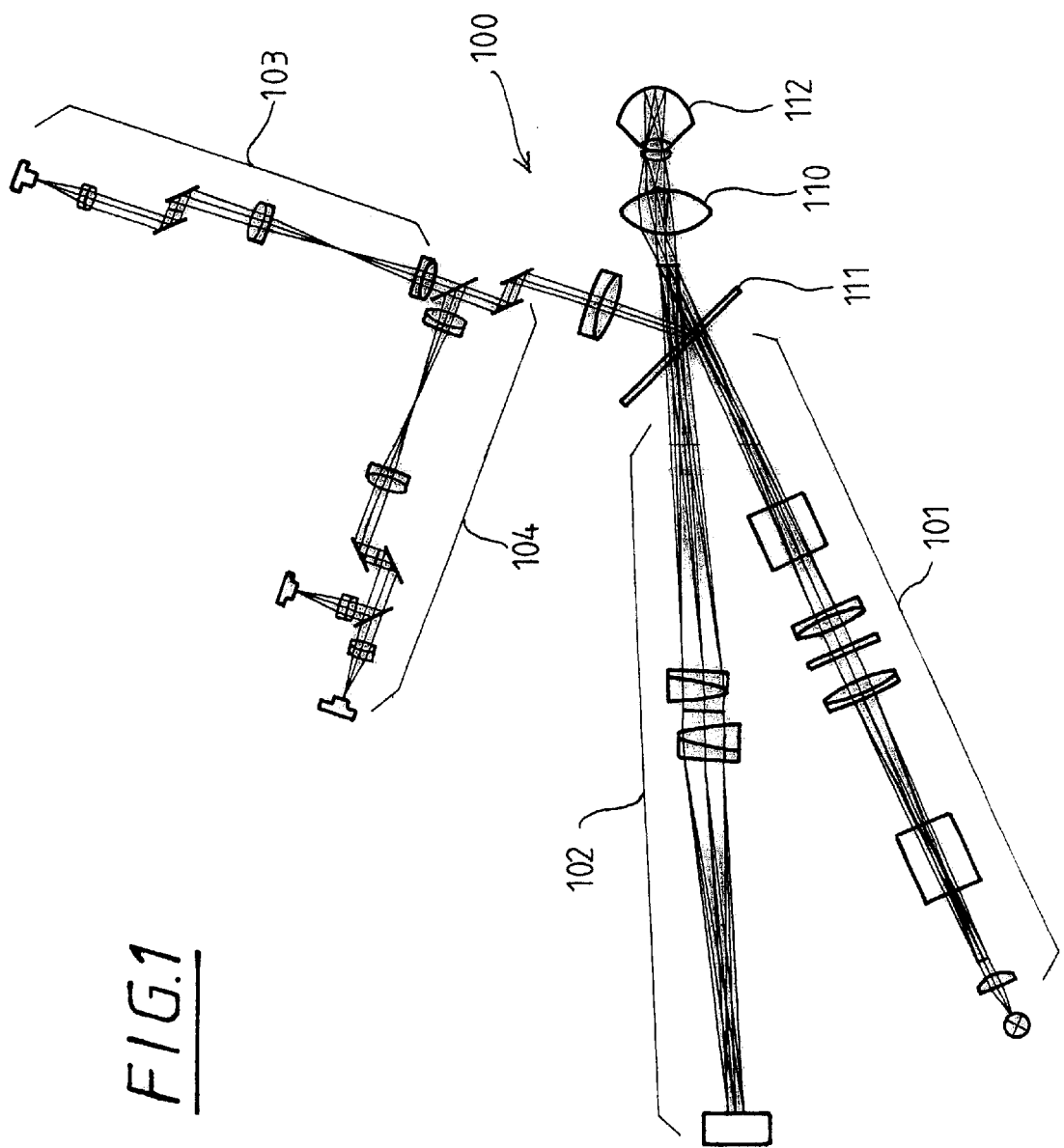
FIG. 1 shows a diagram of a portion of an embodiment of the present invention, and various optical paths associated therewith.

FIG. 1 shows a diagram of a portion of embodiment 100 of the present invention, and various optical paths associated therewith. As shown in FIG. 1, embodiment 100 comprises fundus illumination apparatus 101, viewing apparatus 102, active tracking system 104, and OCT scanning arm 103 of an OCT apparatus. The rest of the OCT apparatus (not shown) is fabricated in accordance with any one of a number of methods that are well known to those of ordinary skill in the art, and is not shown to make it easier to understand the present invention.

An embodiment of fundus illumination apparatus 101 and an embodiment of viewing apparatus 102 are disclosed in U.S. Pat. No. 5,506,634, which patent is assigned to the assignee of the present application, and which patent is incorporated herein by reference. As seen in FIG. 1, the optical path of fundus illumination apparatus 101 and the optical path of viewing apparatus 102 are combined by beamsplitter 111, and the aerial image is relayed onto the retina of eye 112 by ocular lens 110 and the lens of eye 112.

Figure 2:
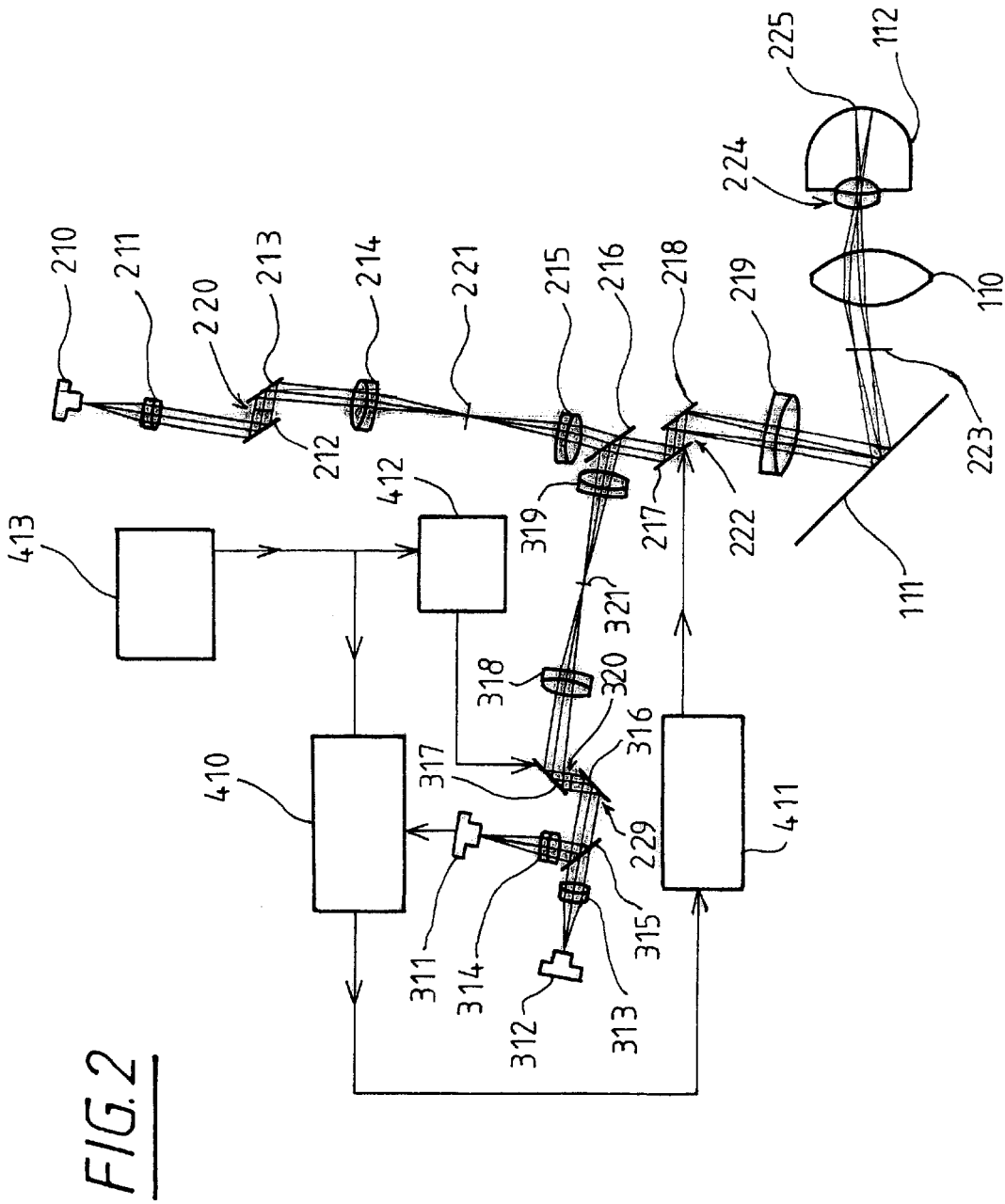
FIG. 2 shows a diagram of a portion of the embodiment shown in FIG. 1 that illustrates an optical path of a beam of tracking radiation output from an active tracking system, and an optical path of a beam of scanning radiation output from an optical coherence tomography ("OCT") apparatus.

FIG. 2 shows a diagram of a portion of embodiment 100, which FIG. 2 illustrates: (a) an optical path of a beam of tracking radiation output from active tracking system 104, and (b) an optical path of a beam of OCT scanning radiation output from OCT scanning arm 103. As shown in FIG. 2, OCT scanning arm 103 comprises a sample arm of an OCT scanning apparatus. In particular, the beam of OCT scanning radiation output from a face end of, for example, fiber interferometer 210, passes through collimating lens system 211 (as is well known to those of ordinary skill in the art, lens system 211 may comprise one or more lenses), and impinges upon scanning mirrors pair 212 and 213 (for example, orthogonally mounted reflectors), which scanning mirrors pair 212 and 213 are driven, for example, by a pair of X-Y galvanometers (not shown for ease of understanding the present invention) in accordance with any one of a number of methods that are well known to those of ordinary skill in the art. As is well known to those of ordinary skill in the art, such OCT scanning radiation is typically output from a short coherence length source such as, for example, a superluminescent diode.

In accordance with this embodiment of the present invention, middle point 220 of scanning mirrors pair 212 and 213 is optically conjugated to middle point 222 of a tracking optical system (embodied, for example, as tracking mirrors pair 217 and 218—for example, orthogonally mounted reflectors) through a one-to-one magnification relay lens system pair 214 and 215 (as is well known to those of ordinary skill in the art, lens system 214 and lens system 215 may each comprise one or more lenses). Tracking mirrors pair 217 and 218 are driven, for example, by a pair of X-Y galvanometers (not shown for ease of understanding the present invention) in accordance with any one of a number of methods that are well known to those of ordinary skill in the art.

As further shown in FIG. 2, a collimated beam of OCT scanning radiation output from scanning mirrors pair 212 and 213 is focused to point 221 by lens system 214. As further shown in FIG. 2, point 221 is optically conjugated to intermediate, aerial image plane 223 through relay lens system pair 215 and 219 (as is well known to those of ordinary skill in the art, lens system 219 may comprise one or more lenses). Still further, aerial image plane 223 is optically conjugated to retina 225 of eye 112 through lens system 110 (as is well known to those of ordinary skill in the art, lens system 110 may comprise one or more lenses) and pupil 224 of eye 112. Finally, middle point 222 of tracking mirrors pair 217 and 218 is optically conjugated to pupil 224 of eye 112 by lens system 219 and lens system 110.

As is well known to those of ordinary skill in the art, scanning mirrors pair 212 and 213 is used to generate a desired scan pattern on retina 225 to form an OCT image. In accordance with this embodiment of the present invention, scanning mirrors pair 217 and 218 comprise a portion of active tracking system 104, which active tracking system 104 is driven by a position error signal detected by tracking electronics 410 in a manner to be described in detail below. A typical OCT scan pattern in a direction perpendicular to the axial scan direction is a line or a circle. In such a case, in accordance with this embodiment of the present invention, scanning mirrors pair 212 and 213 is activated to produce a scan pattern which is a line or a circle. As will be described in detail below, the operation of scanning mirrors pair 212 and 213 is independent of a tracking signal. In accordance with this embodiment of the present invention, if eye motion is detected by active tracking system 104, tracking mirrors pair 217 and 218 will move to follow the eye motion quickly. Since the OCT scanning radiation also passes through tracking mirrors pair 217 and 218, advantageously in accordance with this embodiment of the present invention, the OCT scan pattern is moved together with the eye motion. As a result, the OCT scan position is relatively unchanged with respect to reference tracking features on the retina.

As shown in FIG. 2, an embodiment of active tracking system 104 comprises radiation source 312 which is, for example and without limitation, a laser or a light emitting diode ("LED"), or any one of a number of other coherent or incoherent sources of radiation. A beam of tracking radiation output from tracking beam source 312 is collimated by collimating lens system 313 (as is well known to those of ordinary skill in the art, lens system 313 may comprise one or more lenses), and the collimated beam of tracking radiation passes through beamsplitter 315 and impinges upon dither mechanism 329. Dither mechanism 329 comprises, for example, a pair of orthogonally mounted galvanometers operatively connected to reflectors (galvanometers with low armature inertia can be used to achieve a high-speed tracking response). As further shown in FIG. 2, dither mechanism 329 comprises X-axis and Y-axis dithering mirrors pair 316 and 317 that are driven by a pair of resonant scanners, respectively (not shown for ease of understanding the present invention). In accordance with this embodiment of the present invention, middle point 320 between dithering mirrors pair 316 and 317 is optically conjugated by one-to-one magnification relay lens system pair 318 and 319 (as is well known to those of ordinary skill in the art, lens system 318 and lens system 319 may each comprise one or more lenses) to middle point 222 of tracking mirrors pair 217 and 218. As was described above, middle point 222 of tracking mirrors pair 217 and 218 is optically conjugated to pupil 224 of eye 112. Thus, scanning pivot point 220 and dithering pivot point 320 are optically conjugated to pupil 224 of eye 112. As a result, as was described in U.S. Pat. No. 5,5506,634, there will be no vignetting in the OCT scan beam.

In accordance with this embodiment of the present invention, the tracking radiation is focused by lens system 318 to point 321, and point 321 is optically conjugated, in turn, to retina 225 through lens systems 319, 219, 110 and eye 112. As one of ordinary skill in the art will readily appreciate, tracking radiation that impinges upon retina 225 is retro-reflected by retina 225. The retro-reflected tracking radiation is directed (through the same optical path that brought the tracking radiation to eye 112 in the first place) to beamsplitter 315. Beamsplitter 315 directs the retro-reflected tracking radiation to impinge upon lens system lens 314 (as is well known to those of ordinary skill in the art, lens system 314 may comprise one or more lenses), and lens system 314 focuses the retro-reflected tracking radiation upon photodetector 311 (for example and without limitation, a photodiode).

In accordance with this embodiment of the present invention, motion of eye 112 is detected by sensing changes in reflectance (at the wavelength of the tracking radiation) between a reference tracking feature, and its surrounding or adjacent area. The reference tracking feature may be associated with an eye, or it may be a retro-reflecting material. However, many retinal features have a high enough reflectivity contrast with respect to the background area to be suitable for use as reference tracking features. For example, a reference tracking feature comprising an intersection of two blood vessels in the retina presents a relatively dark area when compared to surrounding retinal tissues. As another example, a reference tracking feature comprising the optical nerve head presents a relatively bright disk when compared to surrounding retinal tissues.

In accordance with this embodiment of the present invention, active tracking system 104 projects tracking radiation onto a reference tracking feature in an area that has about the same size as the reference tracking feature on the retina. Then, as eye 112 moves, due to reflectance differences between the reference tracking feature and the surrounding area, the intensity of the retro-reflected tracking radiation detected by photodetector 311 will change. Further, in accordance with this embodiment of the present invention, the direction of motion is detected by detecting changes in reflected radiation intensity, and a tracking signal is generated to drive tracking mirrors pair 217 and 218 to track the motion of eye 112.

In accordance with one embodiment of the present invention, a mechanism for sensing the direction of motion of eye 112 is fabricated in accordance with a mechanism disclosed in U.S. Pat. No. 5,767,941 ("the '941 patent"), which '941 patent is incorporated by reference herein. In accordance with one embodiment of the present invention, active tracking system 104 locks onto a reference tracking feature by inducing small, periodic, transverse oscillations or dithers in the beam of tracking radiation. The beam of tracking radiation may be formed of any wavelength of radiation that can detect changes in reflectance between the reference tracking feature and the surrounding area. In particular, the beam may be formed from radiation output from a light emitting diode or from any one of a number of other incoherent or coherent sources of radiation. Typically, the reference tracking feature is locked onto by the beam of tracking radiation in two dimensions with a circular dither.

In accordance with one embodiment of the present invention, active tracking system 104 includes a dithering mechanism comprised of a first and a second dither driver (dither mechanism 329 shown in FIG. 2) to dither a beam of tracking radiation in a first and a second direction with, for example, an oscillatory motion having a first phase and a second phase respectively (the first and second phases of oscillatory motion may be orthogonal to each other). In this embodiment, the dither mechanism produces a circular dither at the reference feature whenever the oscillatory motions in the first and second directions have identical amplitudes and have a phase difference of 90 degrees. Active tracking system 104 further includes a tracking device (tracking mirrors pair 217 and 218 shown in FIG. 2) to control the position of the beam of OCT scan scanning radiation relative to the reference tracking feature, and to control the position of the beam of tracking radiation relative to the reference tracking feature. The tracking device comprises a first input for accepting a first direction control signal (applied, for example, to a galvanometer driving tracking mirror 217) and a second input for accepting a second control signal (applied, for example, to a galvanometer driving tracking mirror 218). The first and second direction control signals cause the tracking device to move the OCT scan beam in the first and second directions, respectively.

Active tracking system 104 further includes a reflectometer (beamsplitter 315, lens system 314, and photodetector 311 shown in FIG. 2) positioned in an optical path of the retro-reflected tracking radiation to provide a reflectometer output signal having a phase corresponding to the phase of the retro-reflected tracking radiation. Whenever the beam of tracking radiation traverses a region of changing reflectance, a corresponding variation in intensity of the reflectometer output signal occurs. The reflectometer output signal varies synchronously (when appropriately corrected for phase shifts) with the oscillatory motion caused by the dither mechanism.

Active tracking system 104 further includes a signal processor to compare the phase of the reflectometer output signal with the phases of the signals that caused the oscillatory motion, and to generate the first and second direction control signals that are coupled to the first and second inputs of the tracking device, respectively. The first and second direction control signals cause the tracking device to react so that the OCT scanning radiation tracks relative to the reference tracking feature. As set forth in the '941 patent, a tracking velocity of the tracking device is proportional to the product of a dither frequency of the dither drivers of the dither mechanism and a spatial dimension of the reference tracking feature. In an additional embodiment, in accordance with the '941 patent, active tracking system 104 further comprises an offset signal generator operatively coupled to the dither mechanism and to the tracking device to displace the beam of OCT scanning radiation with respect to the beam of tracking radiation by a predetermined distance. Whenever a control signal is input to the tracking device to reposition the beam of OCT scanning radiation, an offsetting de-control signal is input to the dither mechanism. Such an offset de-control signal can increase the speed at which the beam of OCT scanning radiation can be translated from one target to another target. By providing equal and opposite voltages to the dither mechanism and to the tracking device, the beam of OCT scanning radiation can be translated relative to the beam of tracking radiation quicker than the maximum tracking velocity.

In accordance with this embodiment of the present invention, active tracking system 104 shown in FIG. 2 comprises control unit 413 (for example and without limitation, control unit 413 is embodied as a computer such as a personal computer). Control unit 413 sends a message in accordance with any one of a number of methods that are well known to those of ordinary skill in the art to scanner driving electronics 412. The message causes scanner driving electronics 412 to send dither driver signals to dither mechanism 329 to drive the pair of resonant scanners (the pair of resonant scanners, in turn, drive X-axis and Y-axis dithering mirrors pair 316 and 317, respectively) with a cosine waveform and a sine waveform having equal amplitude in accordance with any one of a number of methods that are well known to those of ordinary skill in the art. These dither driver signals cause the tracking radiation to dither in a circular motion.

As shown in FIG. 2, photodetector 311 outputs a photodetector signal in response to the retro-reflected tracking radiation, and the photodetector signal is applied as input to detection electronics 410, for example and without limitation, detection electronics 410 includes a pair of lock-in amplifiers which are fabricated in accordance with any one of a number of methods that are well known to those of ordinary skill in the art. In accordance with the teaching of the '941 patent, detection electronics 410 determines the phase variation between the signals driving the pair of resonant scanners and the photodetector signal in accordance with any one of a number of methods that are well known to those of ordinary skill in the art using inputs from controller unit 413 and photodetector 311. The phase variation may take the form of a first and second phase comparison signal, which first and second phase comparison signals may comprise DC offset voltages that are proportional to the amplitude of the components of the reflectometer output signal that are in phase with the dither driver signals. These DC offset voltages provide vector correction or error voltages that are proportional to the displacement from equilibrium per dither cycle. Detection electronics 410 also includes an integrator which receives the first and second phase comparison signals as input. In response, the integrator produces, as output, a first and a second integrated signal of the first and second phase comparison signals, respectively. Detection electronics 410 also includes an offset signal generator that accepts the output from the integrator, and, in response, produces a first and a second directional control signal which are applied as input to tracking scanner driver electronics 411 to correct for the phase variation caused by the eye motion. In response, tracking scanner drive electronics 411 sends signals to a pair of, for example, X-Y galvanometers to cause them to drive tracking mirrors pair 217 and 218 to track the motion of eye 112.

The required dither frequency depends upon several factors. For example, if the beam of tracking radiation is imaged on the retina of an eye at unit magnification, a 2 KHz dither frequency will correspond to approximately a 50$\mu$ displacement per dither cycle at a target velocity of 10 cm/sec (i.e., greater than 300 degrees/sec in an eye). Such a dither frequency is sufficient to track a beam of OCT scanning radiation with a spot size of approximately 400$\mu$.

Figure 3:
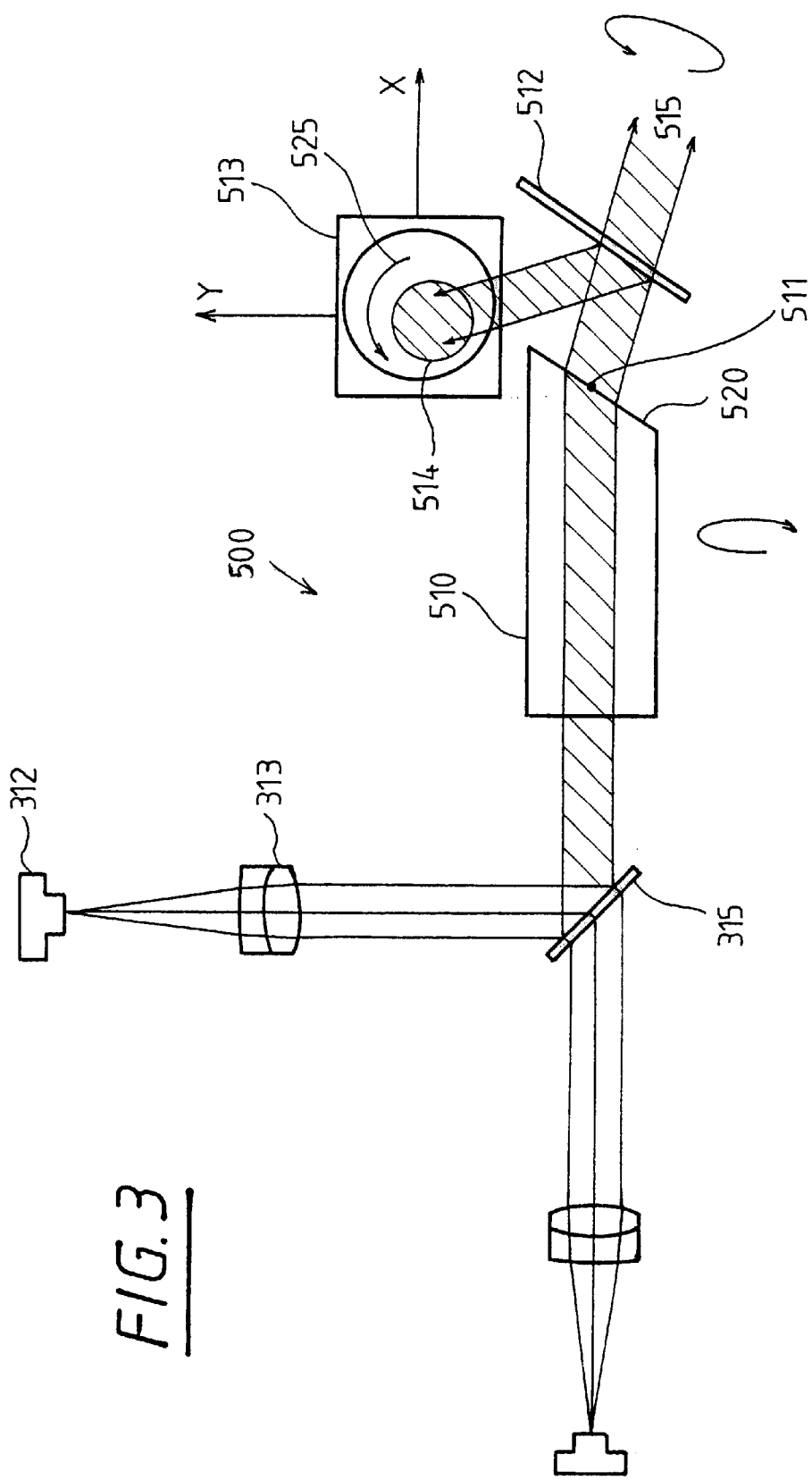
FIG. 3 shows a diagram of a portion of an alternative embodiment of a dither mechanism for use in fabricating an embodiment of the active tracking system shown in FIG. 2.

FIG. 3 shows a diagram of a portion of an alternative embodiment of a dither mechanism for use in fabricating an embodiment of active tracking system 104 shown in FIG. 2. As shown in FIG. 3, a beam of tracking radiation output from tracking beam source 312 is collimated by collimating lens system 313. The collimated beam of tracking radiation passes through beamsplitter 315, emerges as beam 500, and impinges upon dither mechanism 500. As further shown in FIG. 3, dither mechanism 500 comprises wedge prism 510 having a wedge face 520. Wedge prism 510 is rotated about an optical axis of the beam of tracking radiation in a circular motion by a motor (not shown) in accordance with any one of a number of methods that are well known to those of ordinary skill in the art. As a result of rotating wedge prism 510, beam 511 of tracking radiation that emerges from wedge face 520 of wedge prism 510 is dithered in a circular motion. Dithered beam 511 impinges upon beamsplitter 512 and (a) a first portion of dithered beam 511 is directed to impinge onto position sensor 513 and (b) a second portion of dithered beam 511 emerges as dithered beam 515. In accordance with this embodiment of the present invention, point 511 on wedge face 520 of wedge prism 510 is optically conjugated by one-to-one magnification relay lens system pair 318 and 319 (refer to FIG. 2) to middle point 222 of tracking mirrors pair 217 and 218 (shown in FIG. 2). As was described above, middle point 222 of tracking mirrors pair 217 and 218 is optically conjugated to pupil 224 of eye 112. Thus, scanning pivot point 220 and dithering pivot point 511 are optically conjugated to pupil 224 of eye 112.

In accordance with this embodiment of the present invention, position sensor 513 may comprise, for example and without limitation, a silicon position sensor of a type which is well known to those of ordinary skill in the art and which is commercially available. As shown in FIG. 3, the position of beam 514 of tracking radiation rotates, for example, along a path indicated by arrow 525. In accordance with this embodiment of the present invention, beam 514 causes position sensor 513 to generate X-Y signals that are used to measure the phase variation of the retro-reflected tracking radiation intensity for tracking as was described in detail above. The remainder of active tracking system 104 operates in the same manner as does the embodiment described in detail above in conjunction with FIG. 2 where the retro-reflected beam of tracking radiation was directed by beamsplitter 315 toward lens system 314 and photodetector 311.

Those skilled in the art will recognize that the foregoing description has been presented for the sake of illustration and description only. As such, it is not intended to be exhaustive or to limit the invention to the precise form disclosed. For example, although embodiments of the present invention were described in relation to obtaining OCT scan images of an eye, the present invention is not limited thereby, In particular, it is within the scope and spirit of the present invention to encompass method and apparatus for obtaining OCT images of any type of material such as, for example and without limitation, animal, human, and plant tissue.

What is claimed is:

1. An optical coherence tomography ("OCT") application apparatus which performs an OCT application on an object, which OCT application apparatus comprises:

an OCT scanning apparatus which outputs a beam of OCT scanning radiation; and an active tracking system that generates and projects a beam of tracking radiation onto a region including a reference tracking feature, which active tracking system includes a tracking optical system that is disposed to intercept the beam of tracking radiation and the beam of OCT scanning radiation; and wherein the active tracking system analyzes tracking radiation reflected from the region to detect movement of the object, and to generate a tracking signal which directs the tracking optical system to follow the movement of the object.

2. The OCT application apparatus of claim 1 wherein the tracking optical system comprises a pair of orthogonally mounted reflectors.

3. The OCT application apparatus of claim 2 wherein the active tracking system comprises a source of the beam of tracking radiation and a dither mechanism, which dither mechanism causes the beam of tracking radiation to move in a predetermined pattern about the region.

4. The OCT application apparatus of claim 3 wherein the dither mechanism comprises a pair of orthogonally mounted reflectors and wherein a middle point of the pair of orthogonally mounted reflectors is optically conjugated by a one-to-one magnification relay lens system to a middle point of the pair of orthogonally mounted reflectors of the tracking optical system.

5. The OCT application apparatus of claim 4 wherein a middle point of an OCT scanning mechanism of the OCT scanning apparatus is optically conjugated by a one-to-one magnification relay lens system to the middle point of the pair of orthogonally mounted reflectors of the tracking optical system.

6. The OCT application apparatus of claim 5 wherein the middle point of the pair of orthogonally mounted reflectors of the tracking optical system is optically conjugated by one or more lens systems to a target area of the object.

7. The OCT application apparatus of claim 5 wherein:

the OCT scanning mechanism of the OCT scanning apparatus comprises a pair of orthogonally mounted reflectors that are activated to produce a predetermined scan pattern on the object in a direction perpendicular to an axial scan direction; and operation of the OCT scanning mechanism is independent of the tracking signal.

8. The OCT application apparatus of claim 7 wherein the predetermined OCT scan pattern is a line or a circle.

9. The OCT application of claim 4 wherein the pair of orthogonally mounted reflectors are driven by a pair of resonant scanners.

10. The OCT application apparatus of claim 3 wherein the active tracking system: (a) further comprises a photodetector which produces a signal in response to reflected tracking radiation; and (b) analyzes changes in signals output from the photodetector caused, in turn, by changes in intensity of the reflected tracking radiation due to reflectance differences in the region between the reference tracking feature and its surrounding or adjacent area.

11. The OCT application apparatus of claim 10 wherein the dither mechanism causes the beam of tracking radiation to move in a circular pattern.

12. The OCT application apparatus of claim 8 wherein the active tracking system further comprises detection electronics to determine a phase variation between signals driving the dither mechanism to cause the beam of tracking radiation to move in a circular pattern and the signal output from the photodetector.

13. The OCT application of claim 10 wherein the active tracking system further comprises a beamsplitter that directs reflected tracking radiation to impinge upon the photodetector.

14. The OCT application apparatus of claim 10 wherein the source of the beam of tracking radiation comprises one or more of a laser and an LED; and the changes in intensity are determined substantially at wavelengths included in the beam of tracking radiation.

15. The OCT apparatus of claim 10 wherein the active tracking system analyzes the changes in signals output from the photodetector to detect a direction of movement of the object; and generates the tracking signal to drive the pair of orthogonally mounted reflectors of the tracking optical system to follow the movement of the object.

16. The OCT application apparatus of claim 10 wherein the dither mechanism comprises a first and a second dither driver coupled to a pair of orthogonally mounted reflectors that cause the beam of tracking radiation to move in a first and a second direction.

17. The OCT application apparatus of claim 16 wherein the dither mechanism causes the beam of tracking radiation to move in an oscillatory motion in the first direction and in the second direction, the oscillatory motion in the first direction and the second direction having a first phase and a second phase, respectively.

18. The OCT application apparatus of claim 17 wherein the first and second phases of oscillatory motion are orthogonal to each other.

19. The OCT application apparatus of claim 17 wherein the active tracking system further comprises a detection electronics that determines a phase variation between dither driver signals that drive the pair of orthogonally mounted reflectors of the dither mechanism and the photodetector output signal.

20. The OCT application apparatus of claim 19 wherein the active tracking system corrects the photodetector output signal for phase shifts so that the corrected signal varies synchronously with oscillatory motion caused by the dither mechanism.

21. The OCT application apparatus of claim 19 wherein the phase variation comprises first and second phase comparison signals, which first and second phase comparison signals comprise DC offset voltages that are proportional to an amplitude of components of the photodetector output signal that are in phase with the dither driver signals, which DC offset voltages provide error voltages that are proportional to a displacement from equilibrium per dither cycle.

22. The OCT application apparatus of claim 21 wherein the detection electronics further comprises an integrator that receives the first and second phase comparison signals as input, and the integrator produces, as output, a first and a second integrated signal of the first and second phase comparison signals, respectively.

23. The OCT application apparatus of claim 22 wherein the detection electronics further comprises an offset signal generator that accepts the output from the integrator, and, in response, produces first and second directional control signals that are applied as input to tracking scanner driver electronics to correct for phase variation caused by object motion.

24. The OCT application apparatus of claim 3 wherein the active tracking system further comprises an offset signal generator coupled to the dither mechanism and to the tracking optical system to displace the beam of OCT scanning radiation with respect to the beam of tracking radiation by a predetermined distance.

25. The OCT application apparatus of claim 16 wherein the oscillatory motion in the first and second directions have substantially identical amplitudes and have a phase difference of about 90 degrees.

26. The OCT application apparatus of claim 10 wherein the signal output from the photodetector has a phase corresponding to a phase of the reflected tracking radiation.

27. The OCT application apparatus of claim 3 wherein the dither mechanism comprises a wedge prism having a wedge face, which wedge prism is disposed to intercept the beam of tracking radiation on a face opposite the wedge face.

28. The OCT application apparatus of claim 11 wherein the dither mechanism comprises a motor that rotates the wedge prism about an optical axis of the beam of tracking radiation to dither tracking radiation emerging from the wedge face in a predetermined pattern.

29. The OCT application apparatus of claim 28 wherein the dither mechanism further comprises a beamsplitter which directs a first portion of tracking radiation emerging from the wedge face to a position sensor.

30. The OCT application apparatus of claim 29 wherein a point on the wedge face is optically conjugated by a one-to-one magnification relay lens system to a middle point of the pair of orthogonally mounted reflectors of the tracking optical system.

31. The OCT application apparatus of claim 30 wherein a middle point of an OCT scanning mechanism of the OCT scanning apparatus is optically conjugated by a one-to-one magnification relay lens system to the middle point of the pair of orthogonally mounted reflectors of the tracking optical system.

32. The OCT application apparatus of claim 31 wherein the position sensor generates X-Y signals that active tracking system uses to analyze a phase variation of reflected radiation intensity.

33. The OCT application apparatus of claim 2 wherein:
the tracking optical system further comprises a first galvanometer that drives one of the pair of orthogonally mounted reflectors and a second galvanometer that drives the other one of the pair of orthogonally mounted reflectors;
the tracking signal comprises a first direction control signal that is applied as input to the first galvanometer and a second direction control signal that is applied as input to the second galvanometer; and
the first and second direction control signals cause the tracking optical system to move the beam of OCT scanning radiation in a first direction and a second direction, respectively.

34. The OCT application apparatus of claim 1 which further comprises a fundus illumination apparatus and a viewing apparatus.

35. The OCT application apparatus of claim 1 wherein the OCT scanning apparatus which outputs a beam of OCT scanning radiation causes the OCT scanning radiation to scan relatively slowly, whereby a signal-to-noise ratio of images generated by performing such a slow scan is higher that that obtained using a relatively rapid scan.

36. The OCT application apparatus of claim 1 which further comprises an analyzer that receives OCT scanning radiation reflected from the object from the OCT scanning apparatus, which analyzer produces one or more of an image, measurements of retinal and retinal nerve fiber layer thickness, and mapping a topography of an optic nerve head.

37. The OCT application apparatus of claim 1 which further comprises a fundus illumination apparatus and a viewing apparatus.

38. The OCT application apparatus of claim 1 wherein the object is an eye and the reference tracking feature is one of: a reference tracking feature associated with the eye and a retro-reflecting material.

39. The OCT application apparatus of claim 38 wherein the reference tracking feature associated with the eye is one of: an intersection of two blood vessels and an optical nerve head.

40. An OCT application method which performs an OCT application on an object, which OCT application method comprises steps of:
outputting a beam of OCT scanning radiation; and
generating and projecting a beam of tracking radiation onto a region including a reference tracking feature;
disposing a tracking optical system to intercept the beam of tracking radiation and the beam of OCT scanning radiation; and
analyzing tracking radiation reflected from the region to detect movement of the object; and
directing the tracking optical system to follow movement of the object.

41. The method of claim 40 which further comprises dithering the beam of tracking radiation to move in a predetermined pattern about the region.

42. The method of claim 41 which further comprises detecting reflected tracking radiation; and analyzing changes in intensity of the reflected tracking radiation due to reflectance differences in the region between the reference tracking feature and its surrounding or adjacent area.

43. The method of claim 41 wherein the step of dithering comprises rotating a wedge prism having a wedge face, which wedge prism is disposed to intercept the beam of tracking radiation on a face opposite the wedge face.

44. The OCT application apparatus of claim 24 wherein the offset signal generator applies an offsetting de-control signal to the dither mechanism whenever the tracking signal is input to the tracking optical system to reposition the beam of OCT scanning radiation.

* * * * *